(12) United States Patent
Cotton (10) Patent No.: US 9,486,553 B2
(45) Date of Patent: Nov. 8, 2016

(54) METHOD

(75) Inventor: Stephen Cotton, Nottingham (GB)

(73) Assignee: Brightwake Limited, Nottingham, Nottinghamshire (GB)

( * ) Notice: Subject to any disclaimer, the term of this patent is extended or adjusted under 35 U.S.C. 154(b) by 694 days.

(21) Appl. No.: 13/384,086

(22) PCT Filed: Jul. 16, 2010

(86) PCT No.: PCT/GB2010/051164
§ 371 (c)(1),
(2), (4) Date: Jan. 13, 2012

(87) PCT Pub. No.: WO2011/007179
PCT Pub. Date: Jan. 20, 2011

(65) Prior Publication Data
US 2012/0116281 A1    May 10, 2012

(30) Foreign Application Priority Data

Jul. 16, 2009  (GB) .................................. 0912346.4
Dec. 21, 2009  (GB) .................................. 0922263.9

(51) Int. Cl.
*A61F 13/00*    (2006.01)
*A61L 15/60*    (2006.01)
(Continued)

(52) U.S. Cl.
CPC .............. *A61L 15/60* (2013.01); *A61F 13/023* (2013.01); *A61F 13/0283* (2013.01); *A61L 15/26* (2013.01);
(Continued)

(58) Field of Classification Search
CPC ..... A61L 15/26; A61L 15/425; A61L 15/60; C08L 75/04; A61F 13/023; A61F 13/0283; A61F 2013/00676; A61F 2013/00702; A61F 2013/0071; A61F 2013/0077; A61F 2013/00804; A61F 2013/0091; A61F 13/00029; A61F 13/02; A61F 13/0203; A61F 2013/00659; A61F 2013/007
USPC ....................................... 602/41–54; 424/446
See application file for complete search history.

(56) References Cited

U.S. PATENT DOCUMENTS 4,838,253 A    6/1989  Brassington et al.
4,921,704 A *  5/1990  Fabo ............................. 424/446
(Continued)

FOREIGN PATENT DOCUMENTS

EP    0251810 A2   1/1988
EP    1815875 A1   8/2007
(Continued)

OTHER PUBLICATIONS

Great Britain Search Report for GB0912346.4, dated Mar. 25, 2010.
(Continued)

*Primary Examiner* — Michael Brown
(74) *Attorney, Agent, or Firm* — LeClairRyan, a Professional Corporation (57) ABSTRACT

A method of manufacturing a wound dressing or the like comprises the steps of a) providing a layer of substrate material; b) extruding a curable hydrophobic gel precursor composition onto that substrate material via one or more mobile applicators; and c) causing or allowing the hydrophobic gel precursor composition to cure to form a hydrophobic gel. Wound dressings or the like that can be manufactured by such a method comprise a layer of substrate material, the wound facing surface of which carries bands of hydrophobic gel that are intermingled in a lattice-like arrangement.

28 Claims, 4 Drawing Sheets

(51) Int. Cl.
  *A61F 13/02* (2006.01)
  *A61L 15/26* (2006.01)
  *A61L 15/42* (2006.01)
(52) U.S. Cl.
  CPC ...... *A61L 15/425* (2013.01); *A61F 2013/0071* (2013.01); *A61F 2013/0077* (2013.01); *A61F 2013/0091* (2013.01); *A61F 2013/00676* (2013.01); *A61F 2013/00702* (2013.01); *A61F 2013/00804* (2013.01)

(56) References Cited

U.S. PATENT DOCUMENTS

| | | | |
|---|---|---|---|
| 5,167,613 A | 12/1992 | Karami et al. | |
| 5,322,729 A | 6/1994 | Heeter et al. | |
| 5,635,201 A * | 6/1997 | Fabo | 424/443 |
| 5,861,348 A | 1/1999 | Kase | |
| 6,051,747 A | 4/2000 | Lindqvist et al. | |
| 6,277,224 B1 | 8/2001 | Muesch et al. | |
| 7,161,056 B2 | 1/2007 | Gudnason et al. | |
| 2002/0193723 A1 | 12/2002 | Batdorf et al. | |
| 2004/0092855 A1 | 5/2004 | Fabo | |
| 2004/0127835 A1 | 7/2004 | Sigurjonsson et al. | |
| 2004/0181198 A1 | 9/2004 | Farbrot et al. | |
| 2004/0229034 A1* | 11/2004 | Djokic | 428/328 |
| 2005/0003157 A1* | 1/2005 | Shortland et al. | 428/143 |
| 2005/0059918 A1 | 3/2005 | Sigurjonsson et al. | |
| 2005/0215932 A1 | 9/2005 | Sigurjonsson et al. | |
| 2005/0233072 A1 | 10/2005 | Stephan et al. | |
| 2005/0276965 A1 | 12/2005 | Etchells | |
| 2006/0089270 A1* | 4/2006 | Vose | 508/113 |
| 2007/0161056 A1 | 7/2007 | Banerjee | |
| 2007/0293703 A1* | 12/2007 | Chen et al. | 564/177 |
| 2010/0159192 A1 | 6/2010 | Cotton | |
| 2011/0070391 A1 | 3/2011 | Cotton | |

FOREIGN PATENT DOCUMENTS

| | | |
|---|---|---|
| FR | 2609889 A1 | 7/1988 |
| GB | 0713838 | 8/1954 |
| GB | 781975 A | 8/1957 |
| GB | 807276 A | 1/1959 |
| GB | 819635 A | 9/1959 |
| GB | 987275 A | 3/1965 |
| GB | 2153229 A | 8/1985 |
| GB | 2192142 A | 1/1988 |
| GB | 2226780 A | 7/1990 |
| GB | 2423267 A | 8/2006 |
| GB | 2425487 A | 11/2006 |
| JP | 2005314618 | 11/2005 |
| WO | 8705206 A1 | 9/1987 |
| WO | 93/19709 A1 | 10/1993 |
| WO | 93/19710 A1 | 10/1993 |
| WO | 94/17765 A1 | 8/1994 |
| WO | 9961077 A1 | 12/1999 |
| WO | 9961078 A1 | 12/1999 |
| WO | 01/68020 A1 | 9/2001 |
| WO | 2004060225 A1 | 7/2004 |
| WO | 2004108175 A1 | 12/2004 |
| WO | 2005/021058 A2 | 3/2005 |
| WO | 2005034797 A2 | 4/2005 |
| WO | 2006127292 A1 | 11/2006 |
| WO | 2007/025544 A1 | 3/2007 |
| WO | 2007/113597 A2 | 10/2007 |
| WO | 2009/047564 A2 | 4/2009 |
| WO | 2009141640 A1 | 11/2009 |
| WO | 2010061228 A1 | 6/2010 |
| WO | 2010/086457 A1 | 8/2010 |

OTHER PUBLICATIONS

International Search Report for PCT/GB2010/051164, dated Sep. 13, 2010.
"Advances in Pressure Sensitive Adhesive Technology-2," Warwick, Rhode Island: Satas & Associates, 1995.
Product Information Sheet for Dow Corning Soft Skin Adhesives Parts A & B.
Communication of a Notice of Opposition for European Application No. 10734551.4 (May 26, 2015).

* cited by examiner

METHOD

This application is a national stage application under 35 U.S.C. §371 from PCT Application No. PCT/GB2010/051164, filed Jul. 16, 2010, which claims the priority benefit of Great Britain Application Nos. 0912346.4, filed Jul. 16, 2009, and 0922263.9, filed Dec. 21, 2009.

The present invention relates to a method of manufacturing wound dressings.

Different types of wound dressing are required to meet different clinical needs. However, one desirable characteristic common to all wound dressings is that they should be able to be removed from the wound without causing pain and trauma to the patient. In order to meet this requirement, the skin-contacting surface of dressings may be coated with hydrophobic gels, particularly soft silicone gels, which adhere readily to the dry skin surrounding a wound, but do not stick to the moist wound surface itself and therefore do not cause pain or trauma upon their removal. As well as satisfying these principal requirements for use as the skin contact layer, there are several other intrinsic properties of soft silicone that make it particularly advantageous for use in wound dressings. These properties are well-documented and include the fact that silicones are non-toxic, non-allergenic or sensitising, do not shed particles or fibres into the wound, feel soft on the skin and are conformable yet robust.

However, dressings having a continuous gel layer on their skin-contacting surface only allow limited skin breathability and transmission of wound exudate away from the wound site. This necessitates more frequent re-dressing of a wound, which results in increased disturbance of the wound, which delays wound healing. It is therefore desirable to increase the ability of the dressing to transmit moisture away from the wound, which may be achieved by incompletely coating the skin-contacting surface of the dressing with hydrophobic gel. Existing methods for applying an incomplete coating of hydrophobic gel to the skin-contacting surface of dressings involve cutting or punching out sections of either the substrate material of the hydrophobic gel layer. Such methods complicate the manufacturing process and increase production costs, as well as introducing the risk that particles or fragments of material may be created upon cutting, and then become detached in the wound, causing aggravation, a foreign body reaction or formation of an abscess.

The method described in WO2009/047564 overcomes these shortcomings with the use of a rotogravure-type process, where the desired distribution of the hydrophobic gel layer is engraved into a carrier such as a cylinder, which then applies hydrophobic gel in that distribution to the substrate. However, this method is somewhat inflexible and cannot be readily adapted to provide different gel distributions.

There has now been devised an improved method for applying hydrophobic gel to a wound dressing, which overcomes or substantially mitigates the above-mentioned and/or other problems associated with the prior art.

Therefore, according to the first aspect of the invention there is provided a method of manufacturing a wound dressing or the like, comprising the steps of:
a) providing a layer of substrate material;
b) extruding a curable hydrophobic gel precursor composition onto that substrate material via one or more mobile applicators; and
c) causing or allowing the hydrophobic gel precursor composition to cure to form a hydrophobic gel.

The principal benefit of the method of this invention is that it enables hydrophobic gel to be applied to the surface of a substrate in a wide variety of distributions. In particular, this method provides a simple and flexible method for applying a partial coating of hydrophobic gel to the surface of a wound dressing or the like. A partial coating of hydrophobic gel on the skin-contacting surface of a wound dressing or the like is particularly desirable as it enables the transmission of vapours, in particular water vapour, from the surface of the skin, thereby minimising the risk of skin lesions caused by moisture accumulation.

"Wound dressing or the like" is intended to mean a flexible and conformable article that is suitable and intended for application to the skin of a patient for medical purposes. Such articles may include articles that themselves have a therapeutic effect, as well as articles that do not themselves have a therapeutic effect but are intended to retain articles that do.

To improve vapour transmission through the dressing in the regions that are not coated with hydrophobic gel, the substrate is preferably a vapour permeable (ie "breathable") material.

The substrate material preferably has an irregular surface that allows hydrophobic gel to adhere to it effectively. Preferred materials with irregular surfaces are plastic sheet materials such as melt-blown plastics sheets, including melt-blown polyurethane, and foams, such as polyurethane foam.

The substrate may be a breathable film, which is preferably also waterproof, ie liquid-impermeable. Suitable materials include plastic films, particularly polyurethane films. In order to provide for enhanced adhesion of the hydrophobic gel to such a substrate, the plastics film may be bonded to a material having an irregular surface structure, for instance a layer of melt-blown material, eg melt-blown polyurethane, such that the substrate has a two-ply structure. The hydrophobic gel is applied to the irregular material, so that it penetrates into that material and so becomes bonded to that material.

In other embodiments of the invention, the substrate is a layer of absorbent foam material. The foam material is preferably absorbent foam, particularly polyurethane foam.

The thickness of the foam layer may typically be between 1 mm and 10 mm, more commonly between 2 mm and 6 mm, and preferably about 4 mm.

Active ingredients may be incorporated into the foam layer and/or into the layer of hydrophobic gel, either during or after manufacture. Such active agents may include agents that aid healing, prevent or reduce malodour, minimise pain, or prevent or treat infection. In particular, the foam may include an antimicrobial agent such as silver or honey.

The foam material may carry a layer of liquid-impermeable material on the side opposite to the gel layer. This liquid-impermeable layer acts as a barrier to prevent escape of fluid such as wound exudate from the dressing, thus keeping the outer surface of the dressing dry. The liquid-impermeable layer preferably also covers the exposed foam material around the edges of the dressing, or else the edges are otherwise sealed, eg by compression and/or heat-sealing. To improve vapour transmission, this material is also preferably vapour-permeable. This layer is preferably a liquid-impermeable, vapour-permeable, plastic film, particularly polyurethane film.

The liquid impermeable layer may extend beyond the edges of the foam material, forming a border around the pad. In this case, the skin-facing surface of the border is coated with adhesive, such as acrylic adhesive, so when the dressing is applied to a patient the liquid impermeable layer adheres to the skin around the periphery of the foam pad.

This provides a dressing that adheres more strongly to the skin and more effectively seals the wound site, preventing wound exudate escaping or contaminants entering the wound. In this embodiment it is particularly preferable that the liquid impermeable layer is a vapour permeable material, such as polyurethane film.

The curable hydrophobic gel precursor composition is preferably a curable silicone gel precursor composition. Silicone gels that are suitable for forming the skin-contacting surface of a wound dressing may be formed by a reaction between two components that are mixed to form a curable precursor composition. Suitable components that are intended for such reaction to form a curable precursor composition are readily available commercially. Typically, the precursor composition is formed of a mixture of a vinyl substituted silicone and a hydride-containing silicone.

The properties of a hydrophobic gel may be modified by varying the proportions or nature of the components of the precursor composition. For example, the molecular weights of the various components and/or their degree of substitution by reactive groups may be different.

The properties of silicone gels that make them suitable for use on the skin-contacting surface of a wound dressing are well-documented. In particular, silicone gels exhibit excellent releasable adhesion to the skin, and this and other advantages and benefits of skin contact layers comprising layers of silicone gel are particularly well-documented for wound dressing applications. For example, silicone gels are soft, tactile and conformable. They exhibit good adhesion to dry skin and, particularly importantly, low adherence to an underlying wound. Thus, the dressing can be applied to a wound and subsequently removed without causing trauma to the wound. Silicone gels are adhesive but do not leave fibres, residue or tack when removed.

According to the method of this invention, the precursor composition is applied to the substrate via one or more mobile applicators. Each applicator generally comprises a housing having one or more inlet ports, into which the precursor composition enters the applicator, and one or more outlet ports, through which precursor composition is dispensed from the applicator. There are generally multiple outlet ports on each applicator, so the precursor composition can be simultaneously dispensed onto multiple regions of the substrate surface.

The precursor composition is generally supplied to the one or more applicators via a supply conduit. The supply conduit must generally be able to accommodate the motion of the applicator to which it is connected. This is preferably achieved by forming the conduit from a flexible material, such as a flexible plastics material.

Where multiple outlet ports are present, it is preferable that the one or more applicators further comprise an internal reservoir that is in communication with all inlet and outlet ports, such that precursor composition entering each applicator passes into the reservoir before it exits the applicator via the outlet ports. This ensures that the pressure of the precursor composition is even across all outlet port, so the precursor composition is dispensed evenly from each.

The housing of each applicator may be any desired shape that enables the application of precursor composition onto a substrate in the required distribution. However, in preferred embodiments of this invention, the housing is elongate and in particular is cylindrical.

The outlet ports may be arranged regularly or irregularly on the surface of the housing. However, in preferred embodiments of this invention, the outlet ports are regularly spaced and arranged in a single straight row.

The motion of the one or more applicators is generally brought about by an actuation means that is coupled to each applicator. Although the actuation means may take any form that is capable of bringing about the motion of the one or more applicators, it is preferably carried out by a precise mechanical means preferably under the control of a computer to ensure the accuracy and repeatability of the process.

The motion of the one or more applicators may take any form that enables the application of the precursor composition onto a substrate in the desired distribution. The motion is preferably of the whole of the applicator, but may be of only part of the applicator (ie the part of the applicator that carried the outlet ports).

In preferred embodiments of this invention where the one or more applicators are elongate in shape, the one or more applicators preferably oscillate, ie undergo reciprocating motion, along their longitudinal axis.

The method of this invention is preferably carried out as a continuous process on a production line, with the substrate being continuously carried along the line on one or more conveyor belts or the like. In this instance, the applicators are preferably positioned above the production line, dispensing precursor composition onto the substrate surface as the substrate passes along the line.

In a preferred embodiment, the applicator(s) undergo reciprocating motion in a direction that is substantially transverse to the direction of travel of the substrate.

The applicators preferably apply precursor composition to the substrate continuously. Thus, where the substrate is continuously carried along a production line, the precursor composition forms a continuous band on the surface of the substrate as it is dispensed from each outlet port. As the precursor composition as applied to the substrate, the motion of the applicators is preferably such that the bands intermingle and form a lattice-like arrangement. This arrangement is most preferable as, once the precursor composition is cured, the resulting gel layer has greater strength and is less likely to delaminate.

The precursor composition must be of sufficient viscosity to remain substantially in the desired distribution once it has been applied to the substrate. Precursor compositions of insufficient viscosity may spread out following application to the substrate, covering a greater proportion of the substrate surface than is desired. In addition, where the substrate is absorbent foam, the precursor composition must also be of sufficient viscosity to prevent its absorption into the surface of the foam. The viscosity of the precursor composition must also not be so great that it causes complications to the application process, such as clogging of the applicator.

The percentage of the surface area of the substrate that is coated with precursor composition prior to curing is generally 10% to 95%, preferably 40% to 90%, more preferably 50% to 80%, and most preferably 60% to 75%.

Following its application to a substrate, the precursor composition is cured, preferably by exposure to infra-red radiation, generally carried out with the use of medium-wave infra-red heaters. The properties of the resulting hydrophobic gel can be altered by varying the length of time the coated substrate is exposed to the medium-wave infra-red heaters. The exposure time is typically between 5 and 15 minutes. Where the method is carried out as a continuous process, the coated substrate may be carried under banks of infra-red heaters on a conveyor system.

Following curing, the wound dressing material may be left as a single large sheet which can then be cut to size by the patient or medical practitioner, depending on the size and shape of the wound. However, the wound dressing material will generally be cut into a range of sizes following manufacture, to allow for immediate application to a wound. Pre-cut dressings may be further trimmed prior to application, if required.

The wound dressing material may also be incorporated into a composite wound dressing. For example, the wound dressing material may be cut to a suitable size and a liquid impermeable material applied to the surface opposite to the gel layer. This liquid impermeable material may extend beyond the edges of the wound dressing material and be coated with adhesive on its skin-facing surface to provide additional adhesion to the patient when the dressing is applied.

Wound dressings or the like produced according to this invention are generally packaged in individual sterile packaging. Sterilisation may be carried out by exposure to ethylene oxide or by gamma-irradiation, both of which are commonly used to sterilise wound dressings and the like.

A protective release liner is also preferably applied to the hydrophobic gel layer, which may be removed to expose the hydrophobic gel immediately prior to use. The release liner is most preferably formed in such a way as to be readily grasped and removed, eg by having one or more projecting tabs.

Currently preferred embodiments of the invention will now be described in greater detail, by way of illustration only, with reference to the accompanying drawings, in which.

Figure 1:
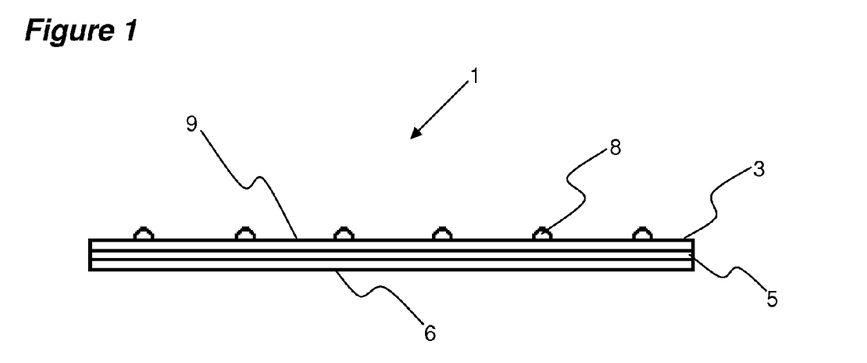
FIG. 1 is a cross-sectional view of the first embodiment of a wound dressing produced according to the method of this invention.

Referring first to FIG. 1, there is depicted a first embodiment of a wound dressing according to the method if this invention, generally designated 1. The dressing 1 is formed of a substrate comprising a liquid impermeable backing layer 6, which is bonded to a layer of melt-blown polyurethane 3 by a layer of acrylic adhesive 5. A layer of hydrophobic gel consisting of a lattice of interwoven gel bands 8 is applied to the melt-blown polyurethane layer 3. The arrangement of the gel bands 8 is not apparent from FIG. 1, but is similar to that shown in relation to other embodiments in FIGS. 2 and 4 below. Uncoated regions 9 of the substrate material are present between the bands 8.

Figure 2:
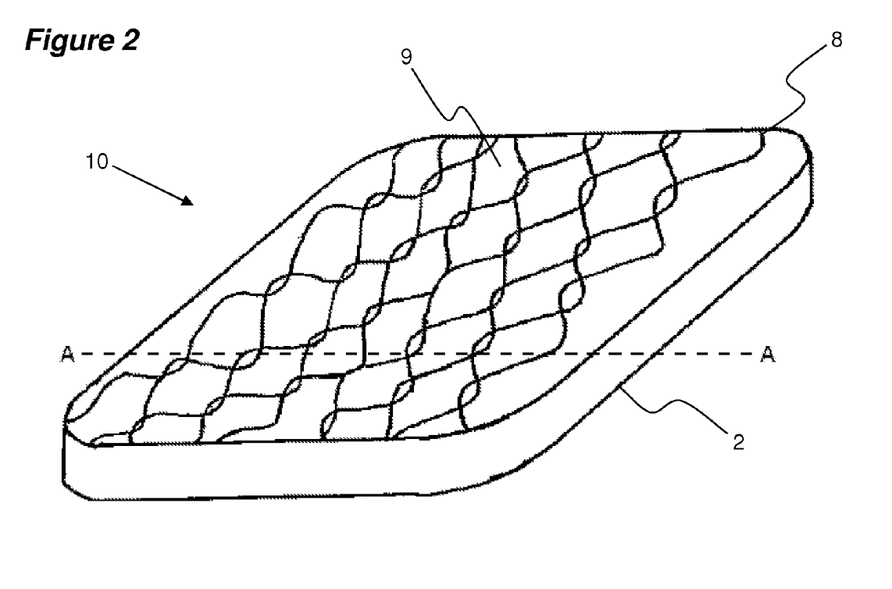
FIG. 2 is a perspective view of a second embodiment of a wound dressing produced according to the method of this invention.
Figure 3:
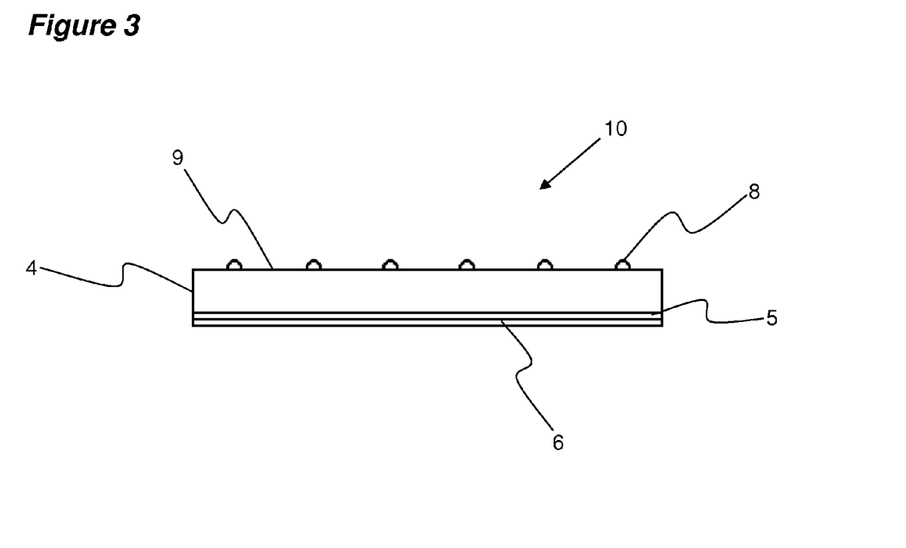
FIG. 3 is a cross-sectional view of the second embodiment of a wound dressing produced according to the method of this invention, taken along axis A-A shown in FIG. 2.

Referring now to FIGS. 2 and 3, there is depicted a second embodiment of a wound dressing produced according to the method of this invention, generally designated 10. The dressing 10 is formed of a substrate 2, comprising an absorbent foam layer 4 with a liquid impermeable backing layer 6 fastened to one surface with a layer of acrylic adhesive 5. The surface of the foam layer 4 opposite the backing layer carries a layer of hydrophobic gel consisting of a lattice of interwoven gel bands 8. Uncoated regions 9 of the foam layer 4 are present between the bands 8.

Figure 4:
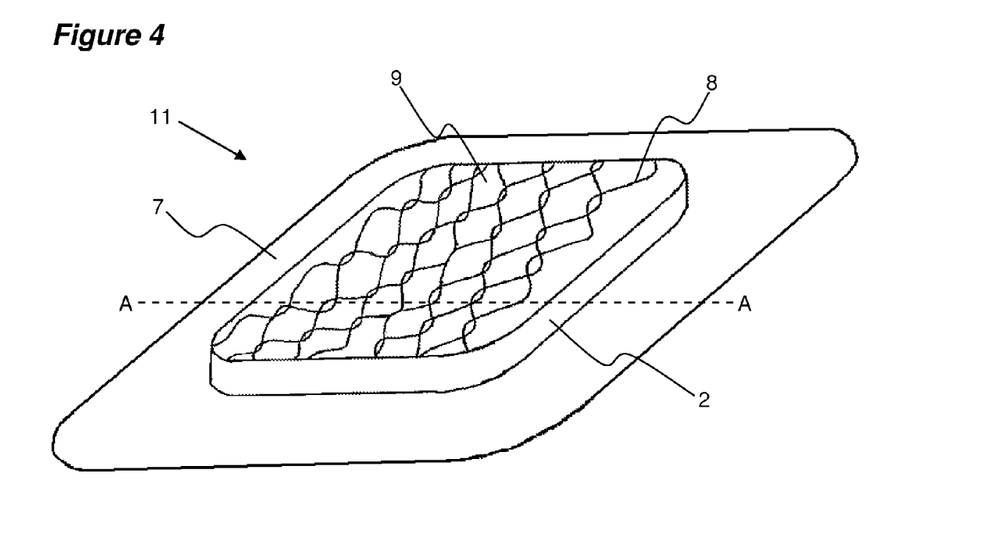
FIG. 4 is a perspective view of a third embodiment of a wound dressing produced according to the method of this invention.
Figure 5:
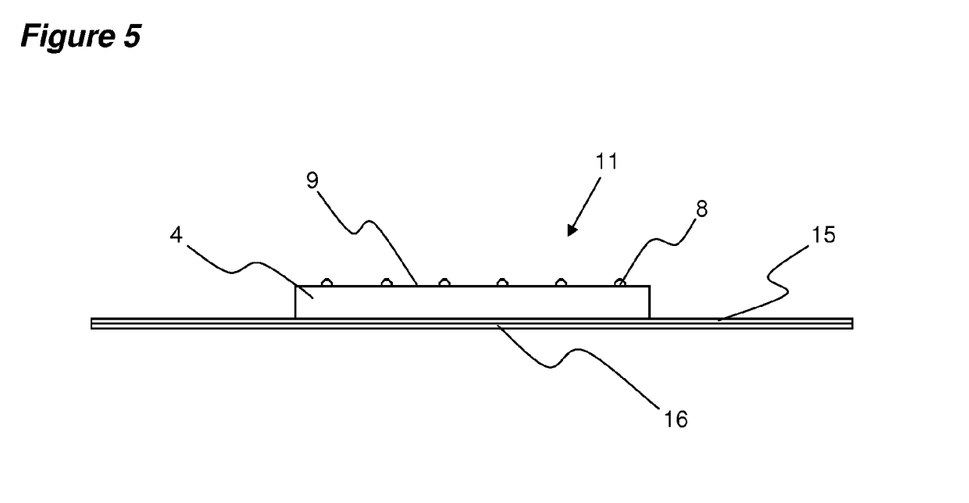
FIG. 5 is a cross-sectional view of the third embodiment of a wound dressing produced according to the method of this invention, taken along axis A-A shown in FIG. 4.

Referring now to FIGS. 4 and 5, there is depicted a third embodiment of a wound dressing produced according to the method of this invention, generally designated 11. The dressing is formed of a substrate 2 comprising an absorbent foam layer 4 having a layer of hydrophobic gel consisting of a lattice of interwoven gel bands 8 on one surface and a liquid impermeable backing layer 16 fastened to the opposite surface with a layer of acrylic adhesive 15. The backing layer 16 extends beyond the edges of the foam layer 4, forming a border 7 around the foam layer 4. The adhesive 15 completely covers one surface of the liquid impermeable backing layer 16 such that the foam pad can be fastened to the centre of the backing layer 16 and the skin-facing surface of the border 7 is coated with adhesive 15. In use, the dressing 11 is applied to a wound such that the silicone coated foam layer 4 covers the wound and the border 7 of the backing layer 16 is adhered to the skin of the patient around the perimeter of the wound to provide stronger dressing adhesion and more effective sealing of the wound environment, preventing the escape of wound exudate or the entry of contaminants into the wound.

Although it should be appreciated that the bands 8 may be formed into any arrangement, including into a parallel, non-intermingling arrangement, a lattice-like arrangement is particularly advantageous as it improves the strength of the gel layer, reducing the chance of delamination.

When in place over a wound, the uncoated regions 9 of the absorbent foam 4 are exposed to the wound surface and are able to absorb wound fluid. This absorption of the wound fluid leads to the expansion of the foam 4 in the uncoated regions 9 into the gaps between the gel bands 8.

Figure 6:
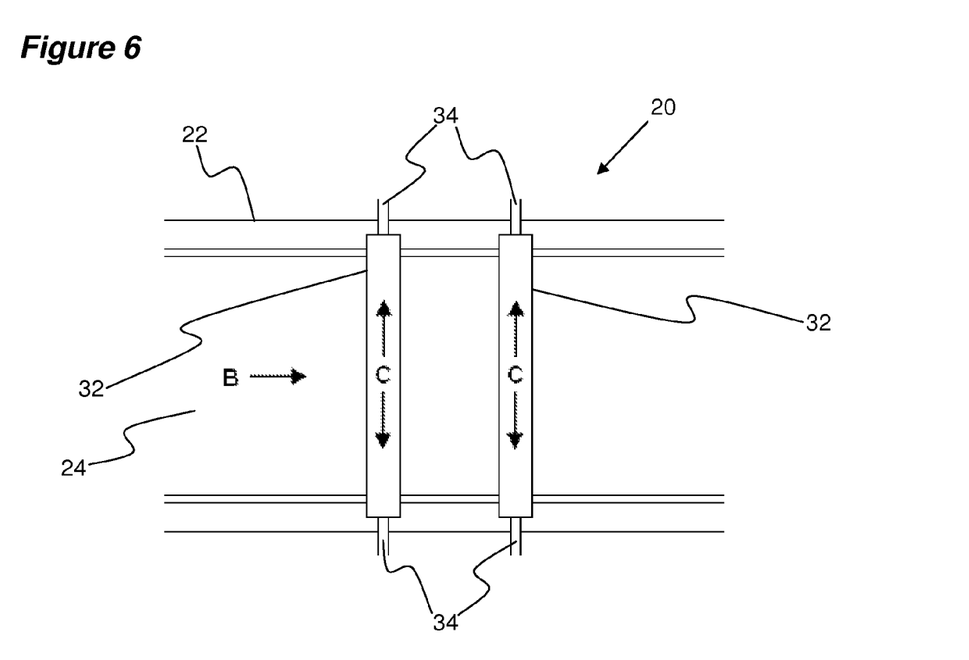
FIG. 6 is a plan view of an apparatus for performing the method of this invention.

FIG. 6 depicts a plan view of an apparatus for performing the method of this invention, generally designated 20. This apparatus 20 comprises a conveyor system 22 having a looped belt 24, and two mobile applicators positioned above the conveyor system 22, each applicator comprising an elongate housing 32 coupled at each end to mountings 34. The motion of the applicators (indicated by arrows C) is brought about by a suitable actuation means (not shown) acting upon the mountings 34. The direction of motion of the conveyor is indicated by arrow B.

Figure 7:
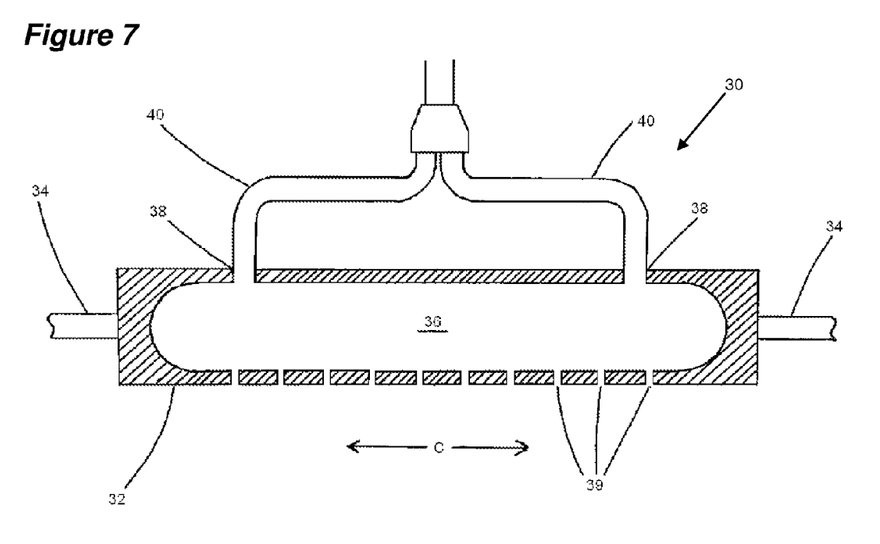
FIG. 7 is a transverse cross-section of a mobile applicator used to perform the method of this invention.

FIG. 7 depicts a longitudinal cross-section of an applicator 30. The applicator 30 comprises an elongated housing 32 coupled at each end to mountings 34. The housing 32 comprises an internal reservoir 36 that communicates with the exterior of the housing 32 via two inlet ports 38 that are connected to supply conduits 40, and a multitude of outlet ports 39.

In use, precursor composition is continuously supplied to the reservoir 36 via the supply conduits 40 and the inlet ports 38, and is dispensed from the reservoir 36 via the outlet ports 39. The introduction of the precursor composition into the reservoir 36 causes the even distribution of pressure throughout the interior of the applicator 30, ensuring the precursor composition is dispensed evenly from each outlet port 39. The rate at which the precursor composition is dispensed from the outlet ports 39 can be altered by varying the rate at which it is supplied to the reservoir 36.

Motion of the applicators 30 (indicated by arrow C) is brought about by any suitable actuation means (not shown) acting upon the mountings 34. This motion takes the form of a continuous oscillation of the applicators along an axis that is transverse to the movement of the conveyor. The motion of the applicators 30 and the conveyor system 22 may be configured such that the bands of precursor composition laid down by one applicator 30 inter mingle with those laid down by the other applicator 30, to give a lattice-like arrangement of bands, as illustrated in FIGS. 1, 2 and 4.

The supply conduits 40 are generally formed of a flexible material to allow their deformation to accommodate the motion of the applicators while the apparatus is in operation.

In operation, a substrate 2, such as a pre-formed laminate consisting of an absorbent foam layer 4 with the liquid-impermeable backing layer 6, is fed along a conveyor 24. Suction may be applied from beneath the belts to hold the substrate 2 flat during at least the initial stages of the manufacturing process.

The upper surface the substrate 2 is coated with the precursor composition as it is transported along the conveyor, via one or more applicators 30, which dispense the precursor composition onto the substrate in a multitude of bands. Although the motion of the applicators may minimal as they apply the precursor composition to the substrate such that the bands of precursor composition that are applied to the substrate are substantially parallel and non-intermingling, the applicators will generally continuously oscillate as they apply the curably mixture, such that the bands of precursor composition are intermingled.

The precursor composition is preferably sufficiently viscous to remain substantially in the distribution in which is it applied to the substrate without spreading to form a continuous layer, or soaking into the foam layer. However, the precursor composition must not be so viscous that it causes complications in the application process, such as clogging of the application apparatus.

The operating parameters may be varied to produce the desired distribution of precursor composition on the surface of the substrate. Variables that may be adjusted include, in particular, the viscosity of the precursor composition, the rate at which the precursor composition is dispensed, the rate of travel of the substrate and the speed and motion of the applicators 30.

The coated substrate then passes into a first curing stage and passes beneath a bank of medium wave infra-red heaters that operate continuously. The thermal energy from these heaters initiates the curing process, and in particular cures the upper surface of the mixture, which maintains the structural integrity of the precursor composition during passage of the substrate through a second, longer curing stage. In the second curing stage, the laminate passes beneath further medium wave infra-red heaters. Curing of the precursor composition, to form a layer of gel of the desired thickness and other properties, is completed during passage of the laminate through the second curing stage. At this stage the power of the infra-red heaters, the speed of passage through the various stages of the process, as well as the length of the curing stages may be varied to suit the particular dressing being manufactured. Typically, the time taken for the laminate to pass through the curing stages is between 5 and 15 minutes.

After completion of curing, a release liner is applied to the exposed surface of the silicone gel layer. This may be achieved by conventional means, involving the feeding of the two components of the release liner from rollers and passing the two components over suitable formers to introduce the fold into the first component and to cause the two components to overlap to the desired extent.

Finally, individual dressings are cut from the assembled laminate, and packaged and sterilised in a conventional manner.

The invention claimed is:

1. A method of manufacturing a wound dressing or the like, comprising the steps of:
   a) providing a layer of substrate material;
   b) extruding a curable hydrophobic gel precursor composition onto an upper surface of the substrate material via one or more mobile applicators such that the upper surface of the substrate material is partially coated with precursor composition, and such that part of the upper surface of the substrate material is not coated with precursor composition; and
   c) causing or allowing the hydrophobic gel precursor composition to cure to form a partial coating of hydrophobic gel on the upper surface of the substrate material, such that part of the upper surface of the substrate material is not coated with hydrophobic gel.

2. A method as claimed in claim 1, wherein the substrate comprises a vapour-permeable, liquid-impermeable film.

3. A method as claimed in claim 2, wherein the substrate comprises a polyurethane film.

4. A method as claimed in claim 1, wherein the substrate comprises an absorbent foam.

5. A method as claimed in claim 4, wherein the foam is polyurethane foam.

6. A method as claimed in claim 4, wherein the foam has a thickness of between 1 mm and 10 mm, or between 2 mm and 6 mm.

7. A method as claimed in claim 4, wherein the foam carries a vapour-permeable, liquid-impermeable layer on the side opposite the gel layer.

8. A method as claimed in claim 7, wherein the vapour-permeable, liquid-impermeable layer is polyurethane film.

9. A method as claimed in claim 1, wherein the curable hydrophobic gel precursor composition is a curable silicone gel precursor composition.

10. A method as claimed in claim 1, wherein the substrate or the hydrophobic gel contains an agent that aids healing, prevents or reduces malodour, minimises pain, or prevents or treats infection.

11. A method as claimed in claim 10, wherein the active ingredient is an antimicrobial agent such as silver or honey.

12. A method as claimed in claim 1, wherein the one or more mobile applicators comprise a housing having one or more inlet ports and one or more outlet ports.

13. A method as claimed in claim 12, wherein the one or more mobile applicators have multiple outlet ports.

14. A method as claimed in claim 12, wherein the one or more mobile applicators further comprise an internal reservoir.

15. A method as claimed in claim 12, wherein the one or more mobile applicators are cylindrical in shape.

16. A method as claimed in claim 12, wherein the outlet ports are regularly spaced and arranged in a single straight row.

17. A method as claimed in claim 1, wherein the one or more mobile applicators are movable through the action of a mechanical actuation means.

18. A method as claimed in claim 17, wherein the one or more mobile applicators are movable in a reciprocating motion.

19. A method as claimed in claim 18, wherein the reciprocating motion is in a direction that is transverse to the direction of travel of the substrate.

20. A method as claimed in claim 1, wherein the method is carried out as a continuous process.

21. A method as claimed in claim 20 wherein the substrate is continuously carried on one or more looped conveyor belts or the like, with the one or more mobile applicators positioned above.

22. A method as claimed in claim 1, wherein the applicators apply the curable hydrophobic gel precursor composition to the substrate continuously.

23. A method as claimed in claim 22, wherein the curable hydrophobic gel precursor composition forms bands on the surface of the substrate.

24. A method as claimed in claim 23, wherein the bands of curable hydrophobic gel precursor composition are intermingled, forming a lattice-like arrangement.

25. A method as claimed in claim 1, wherein the percentage of the substrate surface coated with curable hydrophobic gel precursor composition is between 10% and 95%, or between 40% and 90%, or between 50% and 80%, or between 60% and 75%.

26. A method as claimed in claim 1, wherein the curable hydrophobic gel precursor composition is cured with the use of medium-wave infra-red heaters.

27. A method as claimed in claim 26, wherein the curing process is carried out for between 5 and 15 minutes.

28. A wound dressing or the like, produced by the method of claim 1.

* * * * *